US010881831B2

(12) United States Patent
Khanicheh et al.

(10) Patent No.: US 10,881,831 B2
(45) Date of Patent: Jan. 5, 2021

(54) ENDOSCOPIC BASKET DELIVERY CATHETER

(71) Applicant: HOYA Corporation, Tokyo (JP)

(72) Inventors: Azadeh Khanicheh, Somerville, MA (US); Isaac Ostrovsky, Wellesley, MA (US); Almir Velagic, Watertown, MA (US); Michael Barenboym, Boston, MA (US)

(73) Assignee: HOYA CORPORATION, Tokyo (JP)

( * ) Notice: Subject to any disclaimer, the term of this patent is extended or adjusted under 35 U.S.C. 154(b) by 571 days.

(21) Appl. No.: 15/653,727

(22) Filed: Jul. 19, 2017

(65) Prior Publication Data

US 2019/0022353 A1     Jan. 24, 2019

(51) Int. Cl.
*A61M 25/00*     (2006.01)
*A61M 25/01*     (2006.01)
(Continued)

(52) U.S. Cl.
CPC ....... *A61M 25/0015* (2013.01); *A61B 17/221* (2013.01); *A61M 25/01* (2013.01);
(Continued)

(58) Field of Classification Search
CPC ........ A61M 25/09041; A61M 25/0015; A61M 25/0138; A61M 2025/0024;
(Continued)

(56) References Cited

U.S. PATENT DOCUMENTS 4,988,356 A * 1/1991 Crittenden ........ A61M 25/0169
                                                          600/434
5,334,187 A    8/1994 Fischell et al.
(Continued)

FOREIGN PATENT DOCUMENTS

EP        1096966 A1     5/2001

OTHER PUBLICATIONS

Boston Scientific Corporation, May 2016, "Dreamstone RX Sphincterotome" Brochure, ENDO-377607-AA (6 pages).
(Continued)

*Primary Examiner* — Nathan R Price
*Assistant Examiner* — Melissa A Snyder
(74) *Attorney, Agent, or Firm* — Finnegan, Henderson, Farabow, Garrett & Dunner, L.L.P.

(57) ABSTRACT

Embodiments of the present disclosure are directed to apparatuses, systems, and methods for merging an endoscopic basket delivery catheter onto a fixed guidewire. In one implementation, a catheter may include a sheath having a saddle secured to a distal portion thereof. The sheath may constrain an endoscopic tool such as a basket therein, while the saddle may receive a portion of a guidewire. The saddle may include a slit extending along its longitudinal length. The slit may be widened by a working member of an adapter to allow passage of a locked guidewire into the guidewire lumen of the saddle. The catheter may be merged onto the guidewire via the slit and delivered to the desired treatment device without unlocking of the guidewire. Advantageously, access to at least one desired treatment site may be maintained with the guidewire during merging of the catheter.

20 Claims, 9 Drawing Sheets

(51) Int. Cl.
*A61M 25/09* (2006.01)
*A61B 17/221* (2006.01)
*A61B 17/22* (2006.01)
*A61B 17/3205* (2006.01)
*A61B 17/00* (2006.01)

(52) U.S. Cl.
CPC ........ *A61M 25/0138* (2013.01); *A61M 25/09* (2013.01); *A61B 17/32056* (2013.01); *A61B 2017/0034* (2013.01); *A61B 2017/22038* (2013.01); *A61B 2017/22039* (2013.01); *A61B 2017/22041* (2013.01); *A61M 25/0169* (2013.01); *A61M 2025/0024* (2013.01); *A61M 2025/018* (2013.01); *A61M 2025/0177* (2013.01); *A61M 2025/0183* (2013.01); *A61M 2025/09116* (2013.01)

(58) Field of Classification Search
CPC .... A61M 2025/018; A61M 2025/1056; A61M 25/0169; A61M 25/0097; A61M 25/0136; A61M 2025/0177; A61M 2025/0188; A61M 25/0172; A61B 1/00085; A61B 1/0014; A61B 1/00121
See application file for complete search history.

(56) References Cited

U.S. PATENT DOCUMENTS

| | | | |
|---|---|---|---|
| 6,893,393 B2 * | 5/2005 | Carrillo | A61M 25/02 600/104 |
| 7,172,577 B2 | 2/2007 | Mangano et al. | |
| 7,645,283 B2 | 1/2010 | Reynolds et al. | |
| 8,206,370 B2 * | 6/2012 | von Oepen | A61M 25/0029 604/164.01 |
| 2003/0233043 A1 | 12/2003 | Windheuser et al. | |
| 2005/0059990 A1 | 3/2005 | Ayala et al. | |
| 2007/0129719 A1 | 6/2007 | Kendale et al. | |
| 2009/0212466 A1 | 8/2009 | Boutilette et al. | |
| 2014/0171913 A1 * | 6/2014 | Watanabe | A61M 25/01 604/510 |

OTHER PUBLICATIONS

Boston Scientific Corporation, May 2016, "Trapezoid™ RX" ENDO-333814-AA (4 pages).
Boston Scientific Corporation, Jun. 2016, "Extractor™Pro RX-S" ENDO-396406-AA (2 pages).
U.S. Appl. No. 15/585,487; System and Methods for Device Exchange in an Endoscopic Procedure; Azadeh Khanicheh et al; filed May 3, 2017.
U.S. Appl. No. 15/653,737; Universal Retrieval Device for Removing Obstructions From Body Lumens; Isaac Ostrovsky et al; filed Jul. 19, 2017.
U.S. Appl. No. 15/653,717; Endoscopic Balloon Catheter; Azadeh Khanicheh et al; filed Jul. 19, 2017.
U.S. Appl. No. 15/653,731; Endoscopic Cannulating Devices and Methods of Use; Azadeh Khanicheh et al; filed Jul. 19, 2017.
International Search Report and Written Opinion dated Nov. 6, 2018, by the European Patent Office in PCT/IB2018/055361 (19 pages).

* cited by examiner

ENDOSCOPIC BASKET DELIVERY CATHETER

BACKGROUND

Technical Field

The present disclosure generally relates to endoscopic basket delivery catheters and methods of use. More particularly, and without limitation, the disclosed embodiments relate to apparatuses, systems, and methods for merging a basket delivery catheter onto a guidewire during an endoscopic procedure.

Background Description

Retrieval baskets are commonly used in a variety of endoscopic procedures for removing stones and other bodies from portions of a patient's anatomy. Often, a basket is compressed and received within a catheter for delivery to a desired treatment site. For example, in an endoscopic retrograde cholangiopancreatography (ERCP) procedure, a basket delivery catheter may be introduced over a guidewire through the working channel of a duodenoscope into the biliary tree. The physician or practitioner may advance the basket beyond the distal tip of the catheter, which may cause the basket to assume an expanded configuration. The expanded basket may then be utilized for one or more operations, such as the retrieval and removal of gallstones.

Prior to delivery of the basket via the catheter, access to the treatment site must first be established to achieve placement of the guidewire. Often, a first device such as a cannula or a sphincerotome is introduced through the ampullary orifice (papilla of Vater) and into the biliary tree until the distal end of the first device is proximate to a desired site in the biliary tree. A guidewire is introduced to the treatment site with the first device, and is typically held in place in the endoscope when the first device is removed so that access to the treatment site is maintained. Subsequent devices, such as a basket delivery catheter, may then be introduced over the guidewire and delivered to the treatment site.

Currently, techniques for delivering catheters over guidewires provide the physician limited control of the guidewire. Often, the proximal end of the guidewire must be unlocked from the endoscope and the catheter inserted onto the proximal end of the guidewire. The catheter is then delivered over the guidewire to the treatment site and the guidewire re-locked to the endoscope. This unlocking and re-locking of the guidewire can result in movement or displacement of the distal end of the guidewire and thus loss of access to the treatment site. Additionally, it may be energy- and time-consuming for the physician or practitioner.

Therefore, an improved system or apparatus is needed that allows introduction of a basket delivery catheter over a guidewire which may remain locked or fixed in a desired position during an endoscopic procedure. Such an apparatus or system may be capable of maintaining access to the treatment site during delivery of the catheter and the basket contained therein, and may be capable of reducing the time needed for a physician to perform the endoscopic procedure.

SUMMARY

The embodiments of the present disclosure include apparatuses, systems, and methods for an endoscopic basket and delivery catheter. Advantageously, the exemplary embodiments provide a basket delivery catheter which is easily introduced onto a locked guidewire for delivery of the catheter to a treatment site, where the basket may be expanded and utilized to perform one or more operations.

According to an exemplary embodiment of the present disclosure, a catheter for endoscopic procedures is described. The catheter includes a flexible, elongated sheath and a saddle. The sheath is configured to slidably receive an endoscopic tool therein. The saddle is secured to the sheath. The saddle includes a guidewire lumen configured to receive a guidewire therein. The guidewire lumen includes a slit extending along the length thereof.

According to a further exemplary embodiment of the present disclosure, an apparatus for merging a catheter onto a guidewire is described. The apparatus includes a catheter and an adapter. The catheter includes a flexible, elongated sheath and a saddle. The sheath is configured to slidably receive an endoscopic tool therein. The saddle is secured to the sheath. The saddle includes a guidewire lumen configured to receive a guidewire therein. The guidewire lumen includes a slit extending along the length thereof. The adapter is configured to merge the catheter onto a guidewire. The adapter includes an adapter lumen and a wedge. The adapter lumen is configured to receive the sheath and the saddle. The wedge extends from an inner surface of the adapter lumen. The wedge is configured to widen a portion of the slit such that a portion of the guidewire merges into the guidewire lumen of the saddle through the widened portion of the slit.

According to a yet further exemplary embodiment of the present disclosure, a method for merging a catheter onto a guidewire is described. The method includes obtaining a catheter. The catheter includes a flexible, elongated sheath and a saddle. The sheath is configured to slidably receive an endoscopic tool therein. The saddle is secured to the sheath. The saddle includes a guidewire lumen configured to receive a guidewire therein. The guidewire lumen includes a slit extending along the length thereof. The method additionally includes obtaining an adapter configured to merge the catheter onto a guidewire. The adapter includes an adapter lumen and a wedge. The adapter lumen is configured to receive the sheath and the saddle. The wedge extends from an inner surface of the adapter lumen. The method additionally includes receiving the saddle within the adapter lumen of the adapter such that the wedge engages and widens a portion of the slit. The method additionally includes merging a portion of the guidewire into the guidewire lumen of the saddle through the widened portion of the slit.

According to a still further exemplary embodiment of the present disclosure, a catheter for endoscopic procedures is described. The catheter includes first means for slidably receiving an endoscopic tool and a saddle. The saddle is secured to the first means. The saddle includes a guidewire lumen having second means for receiving a guidewire.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Various disclosed embodiments relate to systems, apparatuses, and methods for improved introduction of a basket delivery catheter onto a guidewire. Various embodiments of the present disclosure may be implemented in an endoscopic system for performing suitable therapeutic operations in one or more desired treatment sites in a patient's anatomy. However, it will be appreciated that embodiments of the present disclosure are not limited to endoscopic applications, and that systems, apparatuses, and methods disclosed herein may be implemented within any suitable diagnostic or therapeutic system. Advantageously, various embodiments of the present disclosure may permit merging of a basket delivery catheter onto a fixed or locked guidewire, thereby maintaining access to at least one desired treatment site.

As described herein, an endoscope typically includes a proximal end and a distal end, and has one or more internal lumens extending between the distal end and the proximal end. A proximal end may refer to a point or a location along the length of the endoscope closer to a physician or a medical practitioner. A distal end may refer to a point or location along the length of the endoscope closer to a diagnosis or treatment site in the body of a patient during an endoscopic procedure. One of the internal lumens of the endoscope may serve as a working channel. One or more tools may be introduced into the working channel from the proximal end of the endoscope to the distal end of the endoscope until a distal end of the tool approximates or reaches a desired diagnosis or treatment site. As described herein, the longitudinal axis of a channel or elongated device may refer to a central axis or an off-center axis of the channel or tubular structure. Exemplary endoscopic tools may include an endoscopic retrieval basket, while may be contained within a delivery catheter.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Figure 1A:
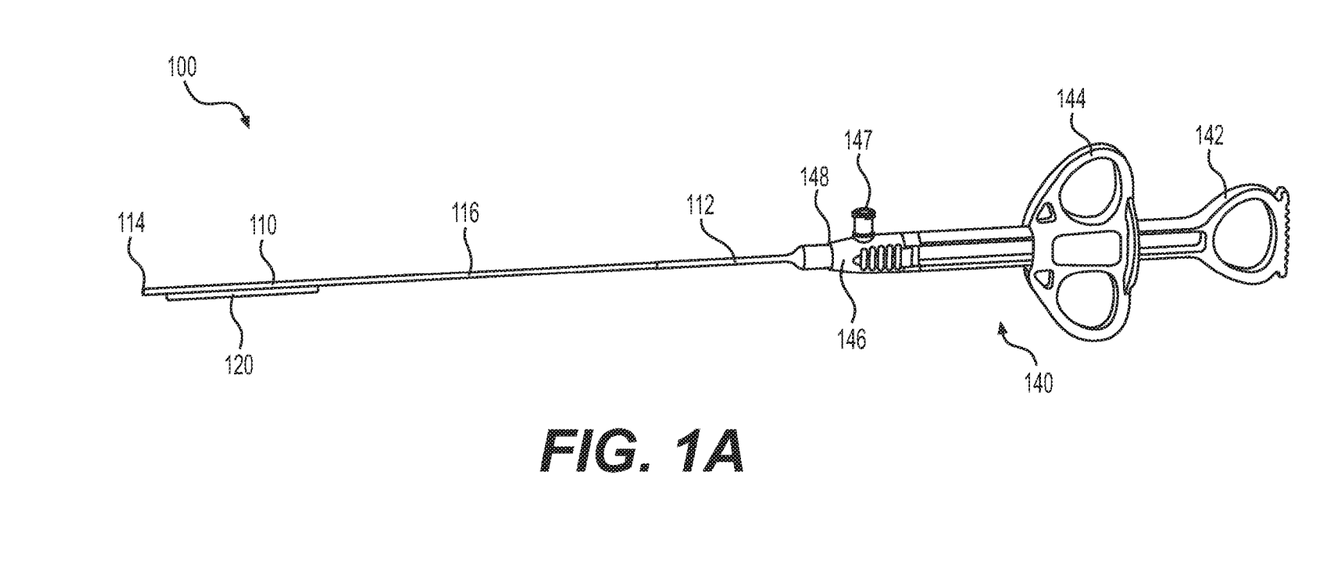
FIG. 1A is a perspective view of an exemplary catheter for delivery of an endoscopic basket, according to embodiments of the present disclosure.

FIG. 1A is a perspective view of an exemplary basket delivery catheter 100. Catheter 100 may include sheath 110, saddle 120, and handle 140. Sheath 110 may be a tubular structure with at least one sheath lumen 212 which extends longitudinally along the entire length thereof. Sheath 110 may be dimensioned to receive an endoscopic tool, such as a retrieval basket, therein. The proximal end of sheath 110 may be received and secured within handle 140, which a user may actuate to control catheter 100 and various components thereof. Saddle 120 may be a tubular structure with at least one guidewire lumen 214 which extends along the entire length thereof. Saddle 120 may be dimensioned to receive a portion of a guidewire therein. Saddle 120 may have a substantially shorter axial length than sheath 110. Saddle 120 may have a longitudinal length of between 5 centimeters and 40 centimeters. According to various embodiments, saddle 120 may have a longitudinal length of between 20 centimeters and 25 centimeters. Saddle 120 may be secured to a distal portion of sheath 110 such that their longitudinal axes are parallel. A proximal portion 116 of the sheath may extend between the proximal end of saddle 120 and handle 140. Sheath 110 may additionally include distal tip 114, which may extend distally beyond the distal end of saddle 120. According to various embodiments, catheter 100 may be dimensioned to be received within a working channel of an endoscope. Sheath 110 and saddle 120 may be constructed of one or more compliant polymeric materials such as PTFE, Pebax, nylon, and polyethylene.

Handle 140 may include grip 142 and actuator 144. Actuator 144 may be connected to the basket received within sheath 110, and may include a pair of finger holes.

Thus, a user may slide actuator 144 distally relative to grip 142 to advance the basket beyond sheath 110. Similarly, the user may slide actuator 144 proximally to retract the basket into sheath 110. Grip 142 and actuator 144 may be configured for single-handed use, in which a physician or practitioner may insert a thumb or a different digit within a thumb hole in grip 142, and may insert two other fingers within the finger holes of actuator 144. Advantageously, this may allow simple control over the advancement and retraction of the basket within sheath 110. Handle 140 may additionally include luer 146. Luer 146 may include injection port 147 and luer outlet 148. Luer outlet 148 may be a narrowed portion of luer 146 within which the proximal end of sheath 110 may be received. Injection port 147 may be fluidly connected with sheath lumen 212, and may be utilized for delivery of fluids, such as contrast, and/or of secondary devices therethrough. Strain relief 112 may be situated about sheath 110.

Figure 1B:
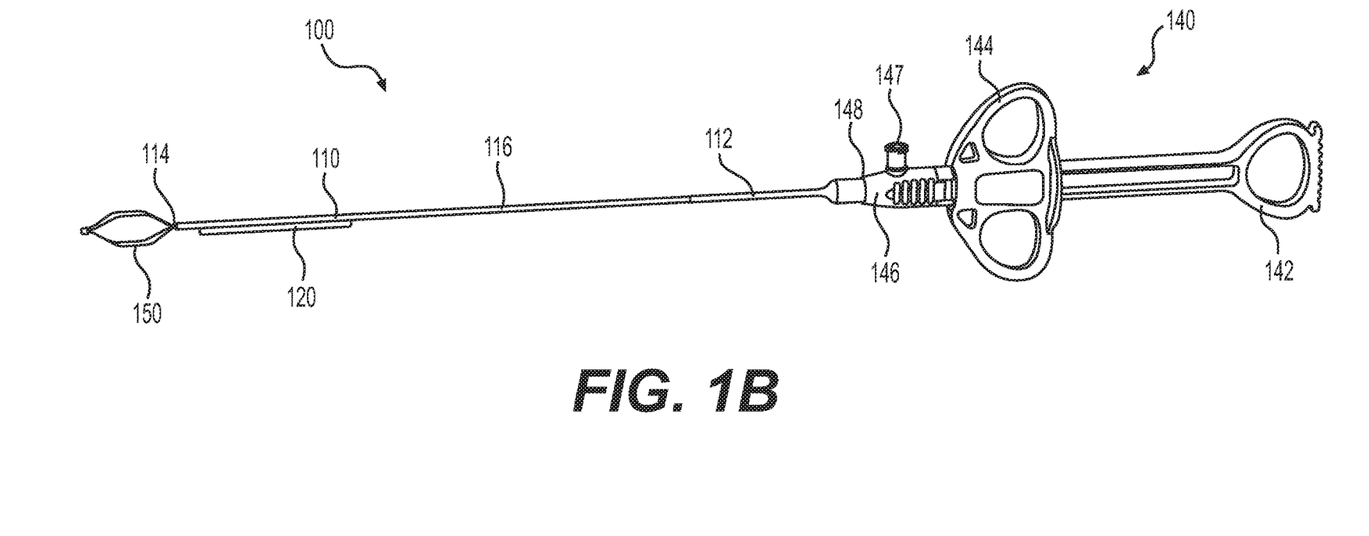
FIG. 1B is a perspective view of the exemplary catheter of FIG. 1A with the basket in an expanded state, according to embodiments of the present disclosure.

FIG. 1B is a perspective view of catheter 100, with basket 150 advanced from distal tip 114. Basket 150 may be slidably received within sheath 110 such that sheath 110 and basket 150 are capable of relative longitudinal movement. Basket 150 may be configured to be withdrawn into sheath lumen 212, and may be deployed by being advanced distally beyond distal tip 114 by actuator 144. When basket 150 is withdrawn within sheath 110, it may assume a closed configuration, such that the inner wall of sheath lumen 212 may constrain basket 150 into a reduced-diameter, compact state. When basket 150 is advanced distally and is no longer constrained by sheath 110, it may assume an open configuration, in which its outer diameter may expand. According to some embodiments, basket 150 may be a self-expanding basket formed from one or more shape memory or superelastic materials, such as stainless steel or nickel titanium. As a result, basket 150 may automatically expand to the open configuration when it is advanced beyond sheath 110. Basket 150 may be connected at its proximal end to a traction member which may extend through sheath 110 to handle 140, where it may connect to actuator 144. The traction member may be a cable, coil, shaft, guidewire, wire, etc.

Saddle 120 may be configured to receive a portion of a guidewire therein. In some embodiments, guidewire lumen 214 of saddle 120 may be lined with a lubricating coating such as PTFE, FEP, or a similar coating. Saddle 120 may have a longitudinal length of between 5 centimeters and 40 centimeters. According to some embodiments, saddle 120 may have a longitudinal length of between 20 centimeters and 25 centimeters. Saddle 120 may have a longitudinal length which is sufficiently short enough to provide catheter 100 with sufficient flexibility for introduction into a tortuous endoscopic working channel. That is, due to the elastic composition, short longitudinal length, and small diameter of saddle 120, catheter 100 is sufficiently flexible for endoscopic use, even in tortuous anatomy.

In some embodiments, a guidewire may be inserted within guidewire lumen 214 of saddle 120 and may be utilized to guide catheter 100 through a working channel of an endoscope to a desired treatment site. Saddle 120, and therefore catheter 100, may slide along the guidewire until catheter 100 reaches the desired treatment site. During this delivery operation, basket 150 may be retained within sheath 110 in the closed configuration. Upon reaching the desired treatment site, basket 150 may be advanced from sheath 110 to assume the open configuration, and may be manipulated by a physician or practitioner for one or more therapeutic operations. For example, basket 150 may be utilized for retrieval of a body such as a stone from the patient's anatomy. In some embodiments, the stone may be fragmented by, for example, a lithotripsy operation, and the fragments may be removed by basket 150. After the therapeutic operation is completed, basket 150 may be retracted into sheath 110 and catheter 100 may be removed from the treatment site via the guidewire.

Figure 2A:
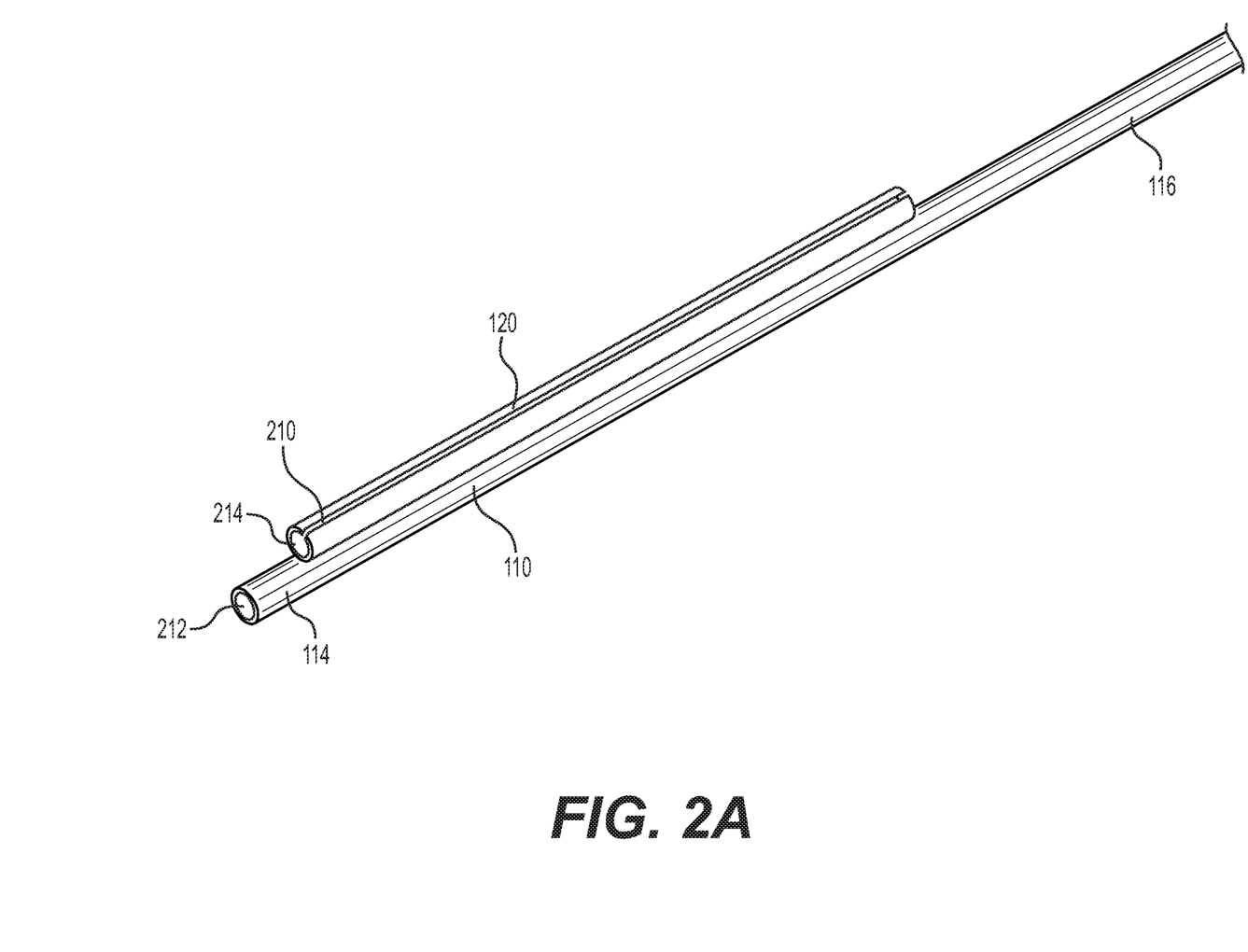
FIG. 2A is a perspective view of a distal end of the exemplary catheter of FIG. 1A, according to embodiments of the present disclosure.
Figure 2B:
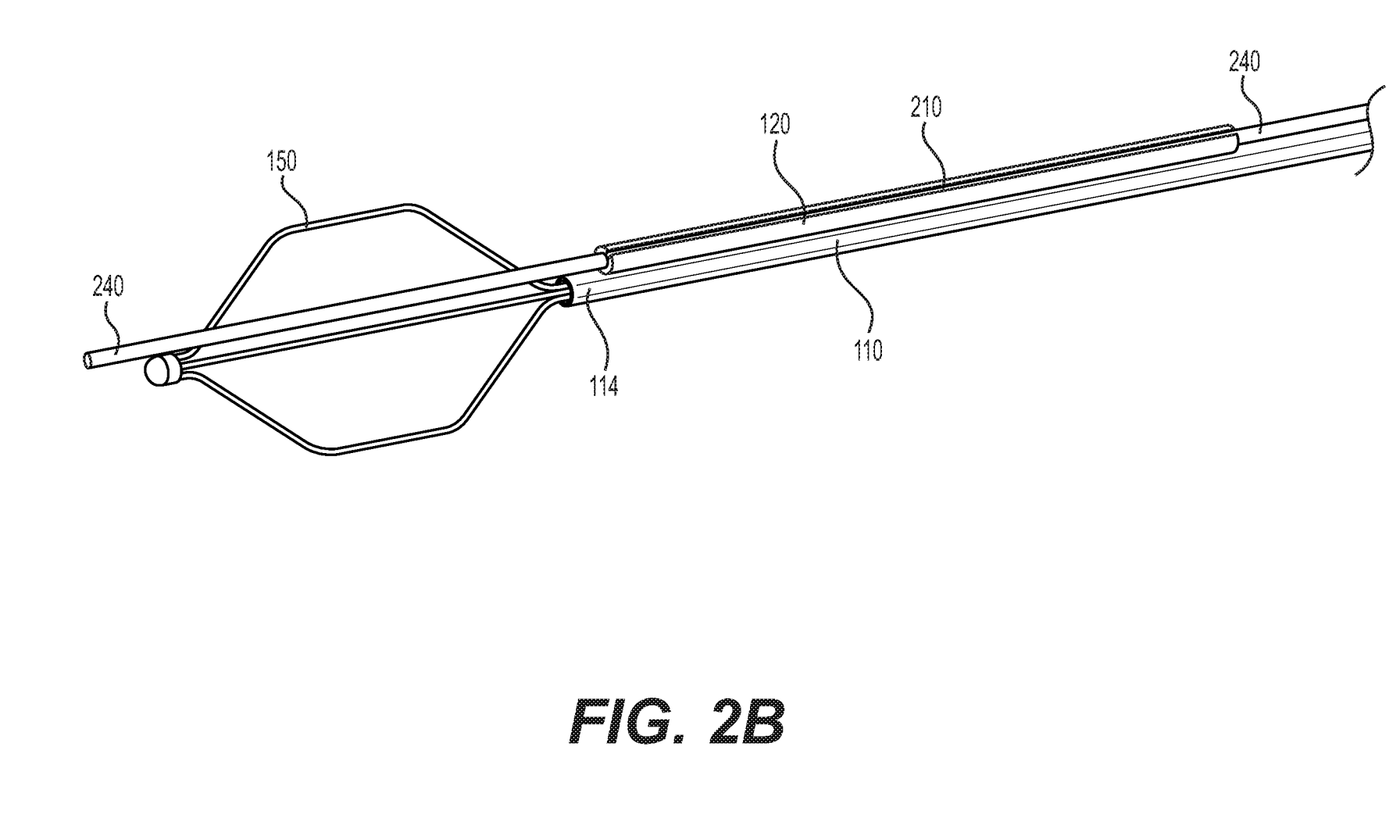
FIG. 2B is a perspective view of the distal end of the exemplary catheter of FIG. 1A with a guidewire received therein and with the basket in the expanded state, according to embodiments of the present disclosure.

FIG. 2A is a perspective view of the distal end of catheter 100. FIG. 2B depicts the distal end of catheter 100 with basket 150 in the open configuration and with a guidewire 240 received within saddle 230. Guidewire 240 may be slidably received within guidewire lumen 214 of saddle 120. In some embodiments, guidewire 240 may be substantially greater in length than saddle 120 such that guidewire 240 extends from the proximal and distal ends of saddle 120. Saddle 120 may additionally include a slit 210, which may extend longitudinally along the entire length of saddle 120. Slit 210 may extend into and merge with a distal opening of guidewire lumen 214, as well as an opening at the proximal end of guidewire lumen 214. Slit 210 may extend radially from guidewire lumen 214 to an exterior surface of saddle 120. Slit 210 may exhibit this radial length along its entire longitudinal length.

Sheath distal tip 114 may include a distal opening of sheath lumen 212. In some embodiments, when basket 150 is advanced from sheath 110, it may emerge from sheath lumen 212 and may assume the open configuration. In some embodiments, basket 150 may be extended until an entire working length thereof has been advanced beyond the distal end of sheath lumen 212. In some alternative embodiments, only a portion of basket 150 is advanced beyond the distal end of sheath lumen 212, with the remainder of basket 150 remaining within the sheath lumen.

Figure 3:
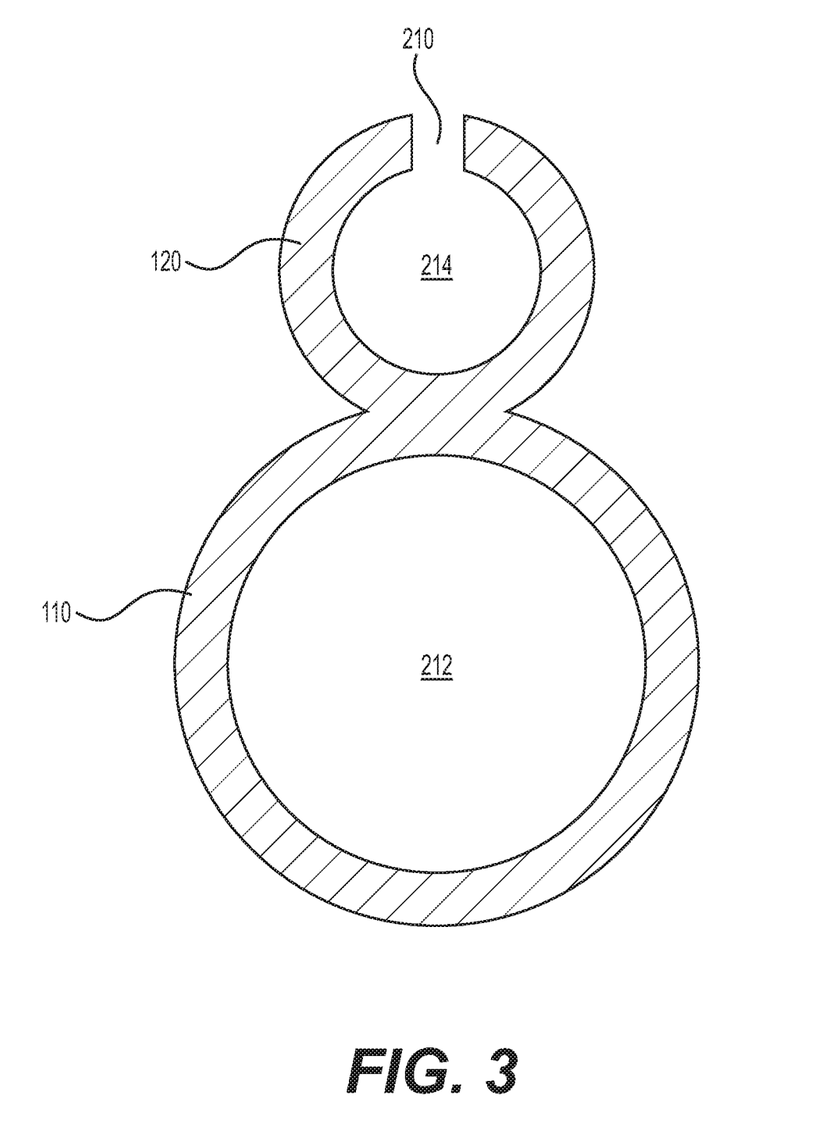
FIG. 3 is a cross-sectional view of the exemplary catheter of FIG. 1A as viewed in a proximal direction, according to embodiments of the present disclosure.

FIG. 3 is a cross-sectional view of catheter 100. Sheath 110 and saddle 120 may be configured as separate tubular structures which may be joined at portions of their respective outer walls. According to some embodiments, sheath lumen 212 may have a larger diameter than guidewire lumen 214. Slit 210 may extend between guidewire lumen 214 and an exterior surface of saddle 210. According to some embodiments, slit 210 may be arranged on saddle 120 at a position which is circumferentially opposite sheath 110. That is, slit 210 may be positioned 180° about the circumference of saddle 210 from sheath 110. Slit 210 may be positioned on a different circumferential portion of saddle 120 in other embodiments.

Slit 210 may have a natural width, which is the width of slit 210 when it is not stretched or flexed. The natural width of slit 210 may be substantially smaller than the diameter of guidewire lumen 214 and the diameter of a guidewire positioned within lumen 214, such as exemplary guidewire 240. As a result, the guidewire may be securely retained within guidewire lumen 214 when slit 210 exhibits its natural width due to the fact that the guidewire cannot pass through the natural width of slit 210. Because of the elastic nature of saddle 120, slit 210 may be stretched or widened beyond its natural width. This widening may occur, for example, due to the application of a widening force by a structure positioned within slit 210. Slit 210 may be stretched to a width equal to or greater than the diameter of guidewire 240. As a result, guidewire 240 may be passed through slit 210 while slit 210 is widened. Slit 210 may re-assume its natural width after the stretching force is removed due to the elastic nature of saddle 120.

In some embodiments, sheath 110 and saddle 120 may be manufactured as separate tubular structures, and may be secured together by one or more of adhesive, heat bonding, laser welding, RF welding, or by other known techniques. In other embodiments, saddle 120 may be manufactured as a two-lumen structure, and sheath 110 may be manufactured as a separate tubular structure. The first lumen of saddle 120 may be guidewire lumen 214, and the second lumen of saddle 120 may be sized to receive sheath 110 therein. According to these embodiments, sheath 110 may be inserted into the second lumen of saddle 120 and secured therein using the aforementioned techniques. Alternatively, other methods may be utilized to construct catheter 100.

Figure 4:
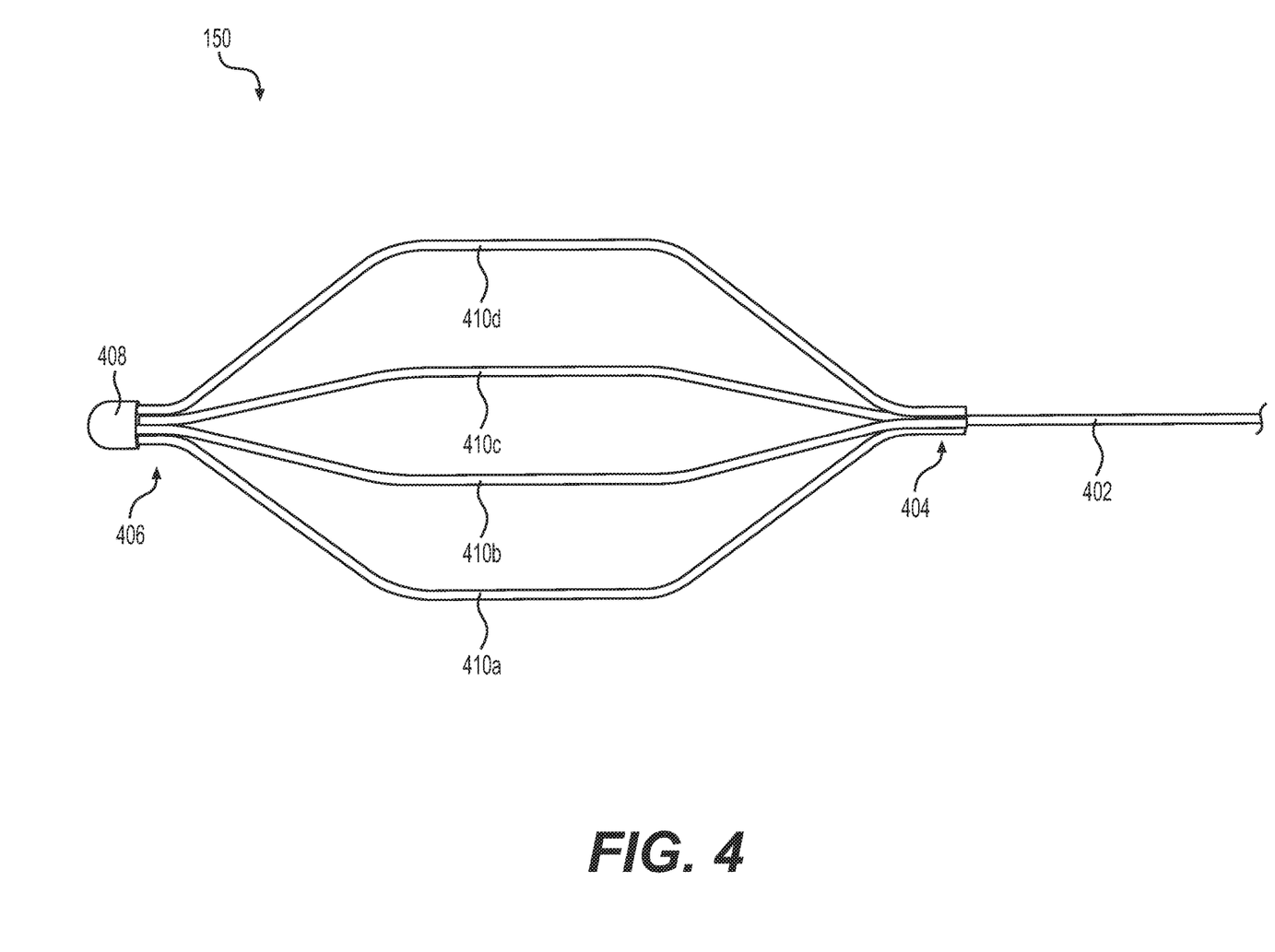
FIG. 4 is a side plan view of the exemplary basket of FIG. 1B, according to embodiments of the present disclosure.

FIG. 4 is a side plan view of basket 150. One of ordinary skill in the art will understand that basket 150 is merely exemplary, and that any suitable endoscopic basket may be used with catheter 100. Basket 150 may contain a plurality of wires 410, such as four wires 410a, 410b, 410c, and 410d. Alternatively, more or fewer wires may be utilized with basket 150. Wires 410 may be evenly spaced to form the desired basket shape. For example, wires 410a-d may be spaced apart by 90°. Wires 410 may extend longitudinally or helically, or may be otherwise curved or bent according to the desired basket shape. Wires 410 may be manufactured of a suitable alloy such as stainless steel or nickel titanium. Wires 410 may converge at distal grouping 406 and at proximal grouping 404. Therefore, the working length of the basket may extend between the two wire groupings, the working length being the large diameter portion of basket 150 which may be utilized for endoscopic procedures. A rounded, atraumatic cap 408 may be positioned at the distal tip of basket 150, about the distal wire grouping 406. Traction member 402 may extend proximally from proximal wire grouping 404 to handle 140 of catheter 100. According to some embodiments, wires 410 are configured to assume the open configuration in which they are expanded to perform an operation such as retrieval of a stone or body. For example, wires 410 may assume the open configuration when no constraining force is exerted upon them, such as the constraining force of sheath 110.

Figure 5A:
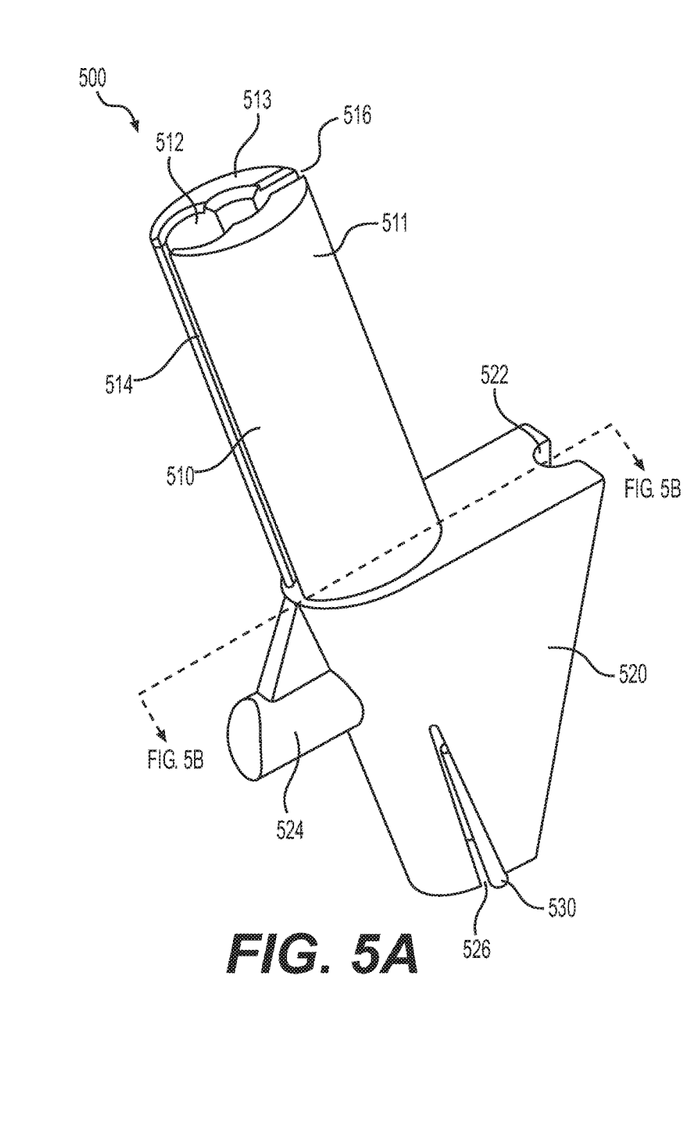
FIG. 5A is a perspective view of an exemplary adapter, according to embodiments of the present disclosure.
Figure 5B:
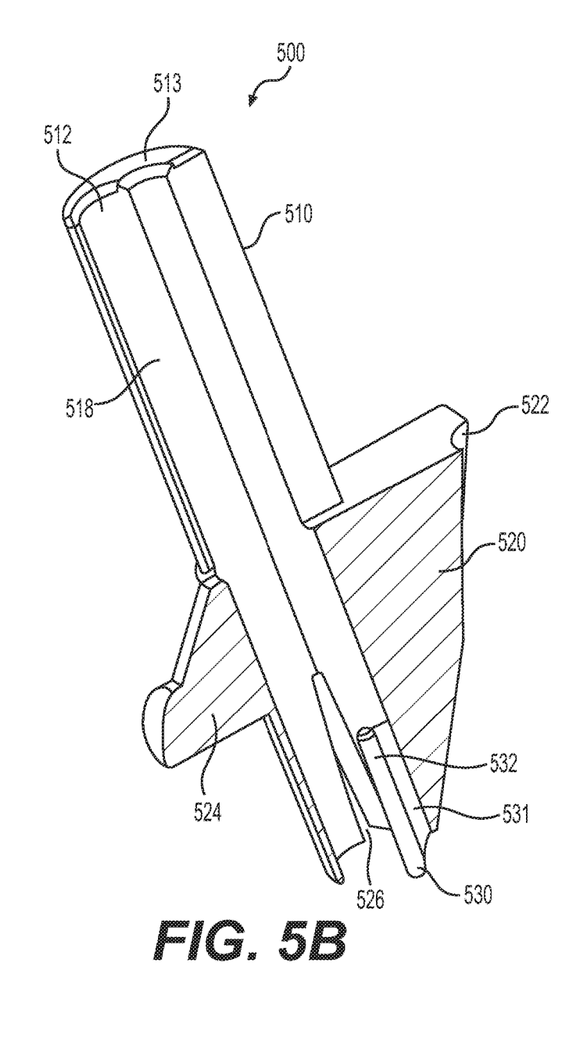
FIG. 5B is a cross-sectional view of the exemplary adapter of FIG. 5A, according to embodiments of the present disclosure.
Figure 5C:
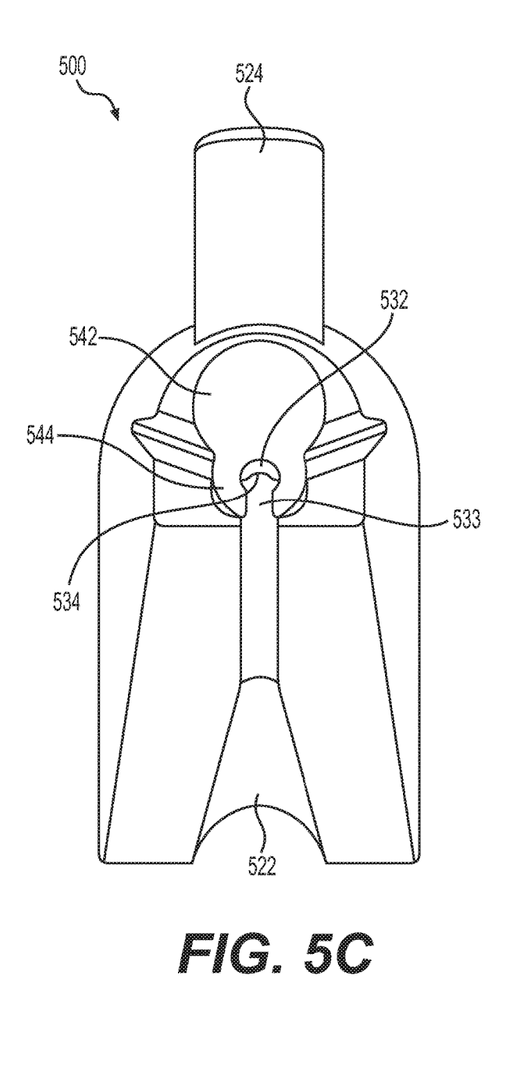
FIG. 5C is a bottom plan view of the exemplary adapter of FIG. 5A, according to embodiments of the present disclosure.
Figure 5D:
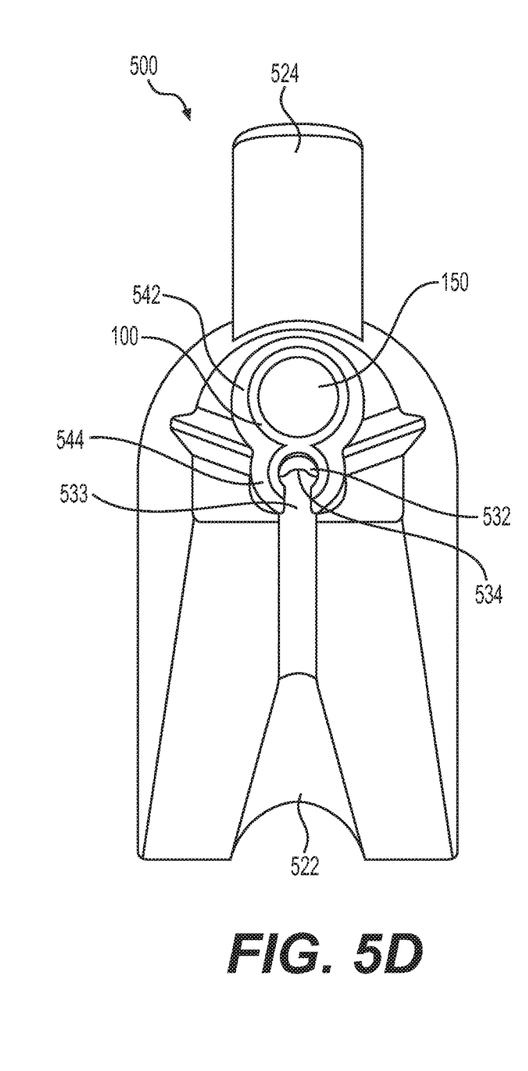
FIG. 5D is a bottom plan view of the exemplary adapter of FIG. 5A with the exemplary catheter of FIG. 1A inserted therein, according to embodiments of the present disclosure.

FIG. 5A is a perspective view of an exemplary adapter 500. FIG. 5B is a cross-sectional view of adapter 500. FIG. 5C is a bottom plan view of adapter 500. FIG. 5D is a bottom plan view of adapter 500 with catheter 100 inserted therein. Adapter 500 may receive catheter 100 therein, including sheath 110 and saddle 120, and may merge saddle 120 onto a guidewire, such as exemplary guidewire 240. Specifically, adapter 500 may receive catheter 100 therein and widen a portion of slit 210. A portion of guidewire 240 may be passed through the widened portion of slit 210 and into guidewire lumen 214 of saddle 120. Catheter 100 may be introduced through the working channel of an endoscope via guidewire 240 until it reaches a desired treatment site.

Adapter 500 may include a tubular portion 510, a body 520, and a working member 530. Tubular portion 510 may be formed as a removable part or an integral part of adapter 500. A working channel 518 may extend longitudinally along the length of adapter 500, including along tubular portion 510 and body 520. Working channel 518 may include an opening 512 at a top end thereof, at the top end of tubular portion 510. Working channel 518 and opening 512 may be configured to receive catheter 100 therein. Slits 514 and 516 may be diametrically positioned within tubular portion 510 and may extend longitudinally along the length of tubular portion 510. Catheter 100 may be visible through slits 514 and 516 when it is positioned within working channel 518.

Tubular portion 510 may include first holder 511 and second holder 513. Holders 511 and 513 may be two deflectable halves of a clamping structure which may be configured to frictionally hold a portion of catheter 100, and may be separated by slits 514 and 516. Holders 511 and 513 may adaptively deflect inward or outward to receive and frictionally clamp onto portions of catheter 100 having different outer diameters. The clamping structure of tubular portion 510 reduces or prevents wiggling of catheter 100 as it passes through working channel 518.

When catheter 100 passes through working channel 518, holders 511 and 513 may frictionally hold at least a portion of sheath 110 and/or of saddle 120, thus securing it in place. Holders 511 and 513 include at least a portion of working channel 518 between them. In some embodiments, the inner surfaces of holders 511 and 513 may be configured to match the outer diameter of at least a portion of catheter 100. For example, the inner surfaces of holders 511 and 513 may form a substantially figure-eight shaped lumen which is substantially the same as the outer diameter of catheter 100 formed by sheath 110 and saddle 120. This allows a portion of catheter 100 to be frictionally held steady (e.g., by preventing catheter 100 from wiggling) as catheter 100 passes through working channel 518 to merge with guidewire 240 (not shown).

As illustrated in FIG. 5C, working channel 518 may be substantially figure-eight shaped. That is, working channel 518 may include two distinct circular portions, with a narrowed portion between them. Working channel 518 may include sheath area 542 as the first circular portion and saddle area 544 as the second circular portion. Sheath area 542 and saddle area 544 may be configured to receive sheath 110 and saddle 120 therein, respectively. In some embodiments, sheath area 542 may have a larger radius than saddle area 544. Working member 530 may extend into saddle area 544 such that it may engage saddle 120 when it is inserted therein.

Working member 530 may be positioned within working channel 518 at an end thereof opposite opening 512. Working member 530 may include a wedge 531 and a guide 532. Wedge 531 may be a thin plate, such as a fin-shaped plate, that stems from the inner wall of working channel 518 and which may be connected with guide 532. Guide 532 may be a tapered cylindrical structure, with a narrow end thereof facing upwards towards opening 512. The body of guide 532 may be parallel to the longitudinal axis of working channel 518. The diameter of guide 532, at any longitudinal portion thereof, may be larger than the width of wedge 531. Working member 530 may open or widen slit 210 of saddle 120 as it passes by, as described further below in reference to FIGS. 7A-7C.

Body 520 may include side groove 522, which may extend along an angled face of body 520 and which may be configured to receive guidewire 240 therein. As illustrated in FIGS. 5C and 5D, a bottom end of side groove 522 may align with wedge 531 and guide 532. Side groove 522 may narrow as it extends towards the bottom of adapter 500. Adapter 500 may additionally include narrowed groove 533, which may extend along the bottom edge of wedge 531 and which may serve as an extension of side groove 522. An angled portion 534 may be situated at the end of narrowed groove 533 and may include a curved body to angle the guidewire inserted therein in a downwards, longitudinal direction. Body 520 may additionally include protrusion 524, which may extend outward from an outer surface of body 520. Protrusion 524 may be generally cylindrical. Adapter 500 may additionally include one or more grooves 526, which may be formed between the outer surface of body 520 and working channel 518.

Figure 6A:
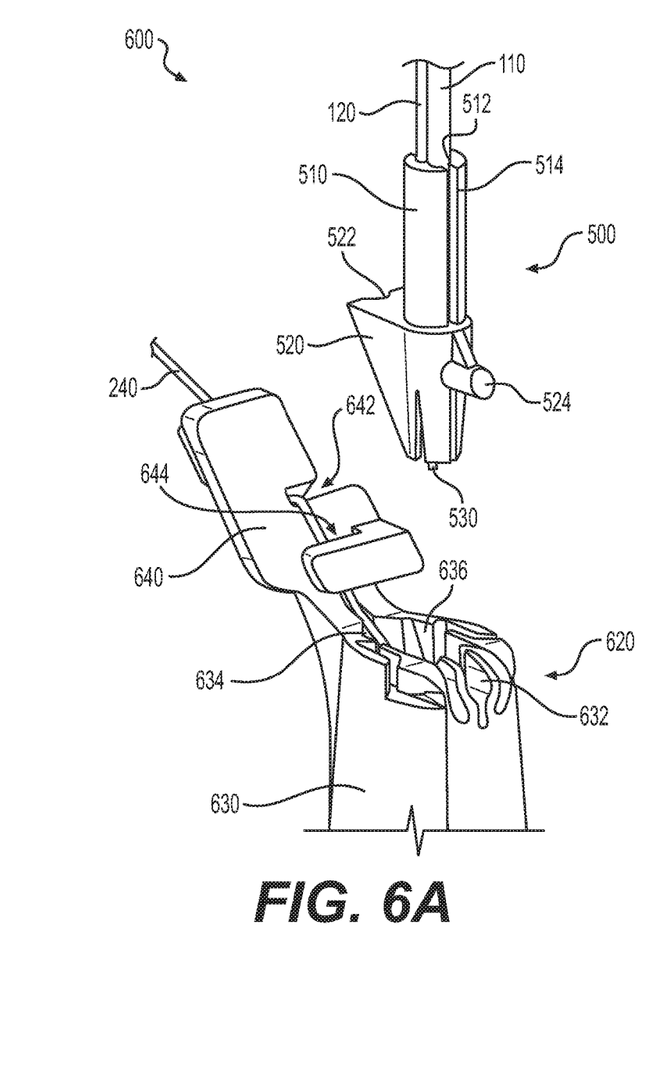
FIG. 6A is a component view of an exemplary system for merging the exemplary catheter of FIG. 1A onto a guidewire, according to embodiments of the present disclosure.
Figure 6B:
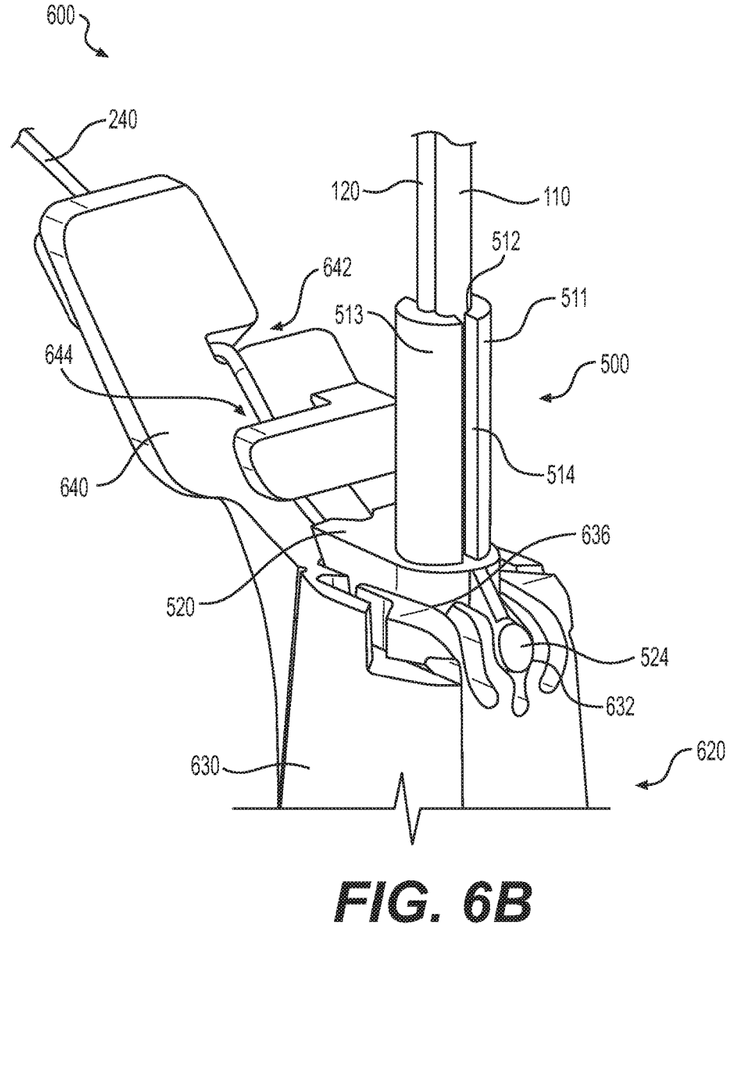
FIG. 6B is a perspective view of the exemplary system of FIG. 6A, according to embodiments of the present disclosure.

FIG. 6A is a component view of an exemplary system 600 for merging catheter 100 onto guidewire 240. FIG. 6B is a perspective view of system 600. System 600 may be used in combination with an exemplary endoscope during an endoscopic procedure. System 600 may include adapter 500, an endoscopic block 620, and at least one catheter 100. Adapter 500 may be fixedly or removably engaged with endoscopic block 620 and may be configured to receive catheter 100 therein such that saddle 120 may be introduced over guidewire 240. Endoscopic block 620 may include a main body portion 630 and a fastener (not shown) which may affix endoscopic block 620 to an exemplary port of the endoscope. The port may be, for example, a biopsy port of the endoscope which may provide access to a working channel of the endoscope. Catheter 100 may be passed through adapter 500 and endoscopic block 620 and into the working channel of the endoscope.

Adapter 500 and endoscopic block 620 may include one or more complementary fitting structures which may allow adapter 500 to fixedly or removably engage with endoscopic block 620. For example, adaptor 500 may removably engage with endoscopic block 620 via frictional fit, threaded fit, snap fit, etc. In some embodiments, body 520 of adapter 500 may be fitted within an opening of a main channel 636 of endoscopic block 620. For example, body 520 may be jammed in the opening of main channel 636, thereby securing adapter 500 on endoscopic block 620. In some embodiments, the user may clamp holders 511 and 513 against catheter 100 during insertion of body 520 into main channel 636, thus securing catheter 100 in place relative to adapter 500. Adapter 500 and endoscopic block 620 may further include other complementary fitting structures. In some embodiments, protrusion 524 of adapter 500 may engage with a clamp 632 of endoscopic block 620. Alternatively or additionally, grooves 526 may engage with complementary protrusions (not shown) in the interior surface of main channel 636. Other suitable mechanical structures may be used alone or in combination with the above-described fitting structures to engage adapter 500 with endoscopic block 620. For example, a detent structure or a fastener may be used to engage adapter 500 with endoscopic block 620. Accordingly, adaptor 500 may be securely held in endoscopic block 620 during the introduction of saddle 120 of catheter 100 over guidewire 240.

Endoscopic block 620 may additionally include a groove 634, which may provide a path for guidewire 240, and a locking device 640 for fixing guidewire 240 in a desired position. Groove 634 may incline from locking device 640 towards the longitudinal axis of main channel 636 such that guidewire 240 is led to be aligned with the longitudinal axis of main channel 636 at a distal end of groove 634. This alignment may permit saddle 120 to be introduced over guidewire 240 as it passes through working channel 518 of adapter 500, as further described below in reference to FIGS. 7A-7C.

More than one guidewire may be received and held in main channel 636. In some embodiments, main channel 636 may include at least one secondary groove for fixing at least one secondary guidewire in a desired position. Guidewire 240 and the secondary guidewire may be held to maintain access to the same treatment site or to different treatment sites, for example. In such instances, endoscopic block 620 may include at least one additional locking device 640 for locking the secondary guidewire in place. In some embodiments, different elongated devices, including catheter 100, may be introduced over guidewire 240 and the secondary guidewire to perform different operations to the same treatment site or to perform different operations to different treatment sites. In other embodiments, the same elongated device, such as catheter 100, may be introduced over guidewire 240 and over the secondary guidewire to perform the same operations to different treatment sites.

Locking device 640 may include zigzag locking features which may fix guidewire 240 in a desired position by frictionally maintaining guidewire 240 in place. For example, the zigzag locking features of locking device 640 may include a plurality of gaps 642 and slots 644. The size of gaps 642 and slots 644 may be approximately the same or smaller than the diameter of guidewire 240 such that guidewire 240 may be frictionally held in place by passing through gaps 642 and slots 644. In some embodiments, the zigzag locking features of locking device 640 may be used in combination with other mechanical features that can bend, twist, pinch, clamp, or lock guidewire 240 in place.

In some embodiments, catheter 100, including sheath 110 and saddle 120, may be passed through working channel 518 of adapter 500 along the longitudinal axis thereof. Guidewire 240 may be merged into slit 210 of saddle 120 when saddle 120 passes by working member 530, which may open or widen slit 210 to receive the nearby portion of guidewire 240 therethrough. When catheter 100 is inserted though working channel 518, the distal tip of saddle 120 may abut and engage the top of working member 530. Wedge 531 may open up or widen the distal end of slit 210, thereby allowing guidewire 240 to merge into slit 210. Wedge 531 also maintains the opening of slit 210 as saddle 120 passes by working member 530, thereby allowing for continuous merging of guidewire 240 into slit 210. Guide 532 may enter guidewire lumen 214 to maintain the direction of insertion of catheter 100 during its merge with guidewire 240. After the portion of slit 210 passes beyond working member 530, it may return to its natural width out of its own elasticity. Catheter 100 may be passed through working channel 518 until the entire length of saddle 120 has been merged onto guidewire 240. The physician or practitioner may continue passing catheter 100 through working channel 518, causing catheter 100 to be passed through endoscopic block 620 and into the working channel of the endoscope. Catheter 100 may then be guided to the desired treatment site by guidewire 240. Catheter 100 may be removed off guidewire 240 by saddle 120 being continuously split or torn away from guidewire 240 through slit 210 while guidewire 240 remains fixed by locking device 640.

In some embodiments, when adapter 500 is engaged with endoscopic block 620, side groove 522 of adapter 500 may complement main groove 634 of endoscopic block 620 to provide a path for leading guidewire 240 towards main channel 636. In some embodiments, side groove 522 may extend up to angled portion 534 of adapter 500 such that guidewire 240 may be directed downwards along the longitudinal axis of adapter 500. This may permit guidewire 240 to be aligned with saddle 120 when catheter 100 passes through working channel 518 along the longitudinal axis of adapter 500, thereby naturally merging into saddle 120 as catheter 100 passes by working member 530 at angled portion 534.

Figure 7A:
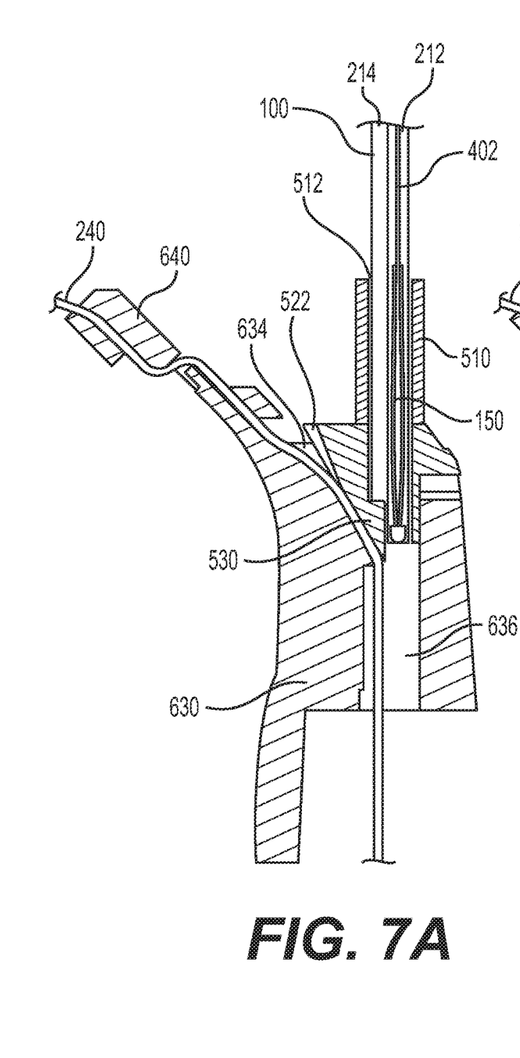
FIG. 7A-7C depict perpendicular cross-sectional views of the exemplary system of FIG. 6A at different stages of merging the exemplary catheter of FIG. 1A onto a guidewire, according to embodiments of the present disclosure.
Figures 7B, 7C:
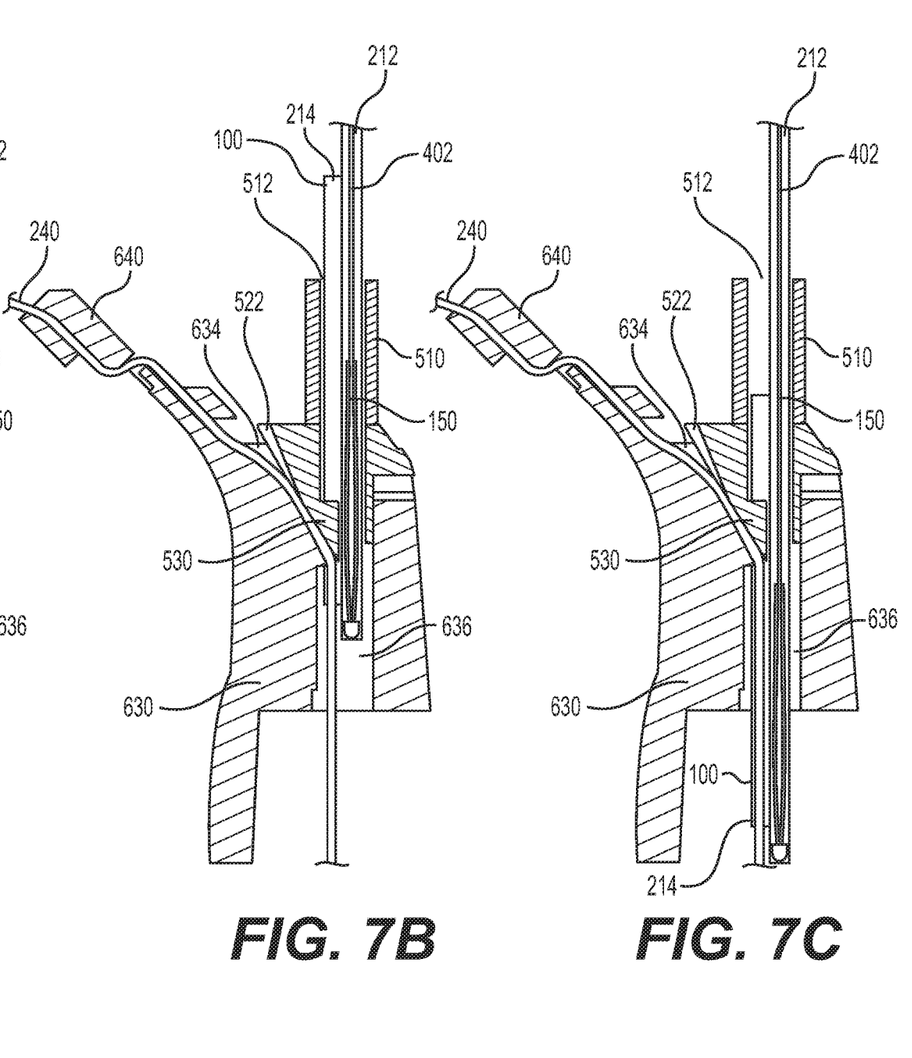

FIGS. 7A-7C are perpendicular cross-sectional views of system 600 at different stages of merging catheter 100 onto guidewire 240. According some embodiments, before introducing catheter 100 over guidewire 240, guidewire 240 may introduced to a treatment site by a first device such as a cannula or a sphincerotome and may be locked by locking device 640 in a predetermined position to maintain access to the treatment site. As shown in FIGS. 7A-7C, after passing through the locking features of locking device 640, guidewire 240 may be received in a path formed by main groove 634 and side groove 522 and led towards angled portion 534 of adapter 500.

As shown in FIG. 7A, to introduce catheter 100 over guidewire 240, a physician or an assistant may insert catheter 100 into working channel 518 of adapter 500. According to some embodiments, catheter 100 may be inserted into adapter 500 prior to insertion of adapter 500 into endoscopic block 620. According to alternative embodiments, adapter 500 may be inserted into endoscopic block 620 prior to insertion of catheter 100 into adapter 500. In some embodiments, to facilitate the alignment of catheter 100 with working member 530 and/or guidewire 240, the inner diameter of working channel 518 may be selected to substantially match an outer diameter of catheter 100. For example, the figure-eight shape of working channel 518 may necessitate insertion of sheath 110 into sheath area 542 and insertion of saddle 120 into saddle area 544, due, at least in part, to the fact that sheath 110 may have a larger outer diameter than saddle 120. As catheter 100 passes through working channel 518, the distal tip of slit 210 meets and passes by working member 530, which then wedges open a portion of slit 210. As shown in FIG. 7B, this in turn allows a portion of guidewire 240 at angled portion 534 to merge into a corresponding portion of saddle 120, e.g., a portion of guidewire lumen 214, through the opened portion of slit 210. After guidewire 240 merges into the distal end of saddle 120, as shown in FIG. 7C, guidewire 240 can continuously merge into saddle 120 as catheter 100 passes though working channel 518 until the entire length of guidewire lumen 214 has been merged onto guidewire 240. In some embodiments, once the entire length of guidewire lumen 214 has been merged onto guidewire 240, the physician or practitioner may continue inserting catheter 100 through working channel 518 and endoscopic block 620 and into the working channel of the endoscope until the distal tip 114 of catheter 100 reaches the desired treatment site. During the insertion process of FIG. 7A-7C, basket 150 may be held within sheath lumen 212. Once catheter 100 reaches the desired treatment site, basket 150 may be advanced and expanded to perform one or more therapeutic operations.

As described above, guidewire 240 is held in place by locking device 640 throughout the merging of guidewire 240 into saddle 120. This advantageously reduces the risk of losing the access to the desired treatment site in the body of a patient and increases the effectiveness of the introduction of catheter 100 over guidewire 240 in a minimum amount of time. Additionally, basket 150 is not disturbed during merging of saddle 120 onto guidewire 240, since basket 150 is retained in a separate tubular portion of catheter 100 than the portion of catheter 100 into which guidewire 240 may be merged.

According to various embodiments, to retrieve catheter 100 introduced over guidewire 240, a physician or an assistant may remove adapter 500 from endoscopic block 620 and pull catheter 100 out of the lumen of the endoscope and main channel 636. Guidewire 240 can remain locked by locking device 640 so that another elongated device may be introduced to the treatment site. During the retrieval of catheter 100, to remove catheter 100 off guidewire 240, the physician or assistant may separate saddle 120 from guidewire 240 by continuously splitting or tearing saddle 120 from guidewire 240 through slit 210.

Exemplary apparatuses, systems, and methods of the present disclosure may provide a number of benefits over prior apparatuses, systems, and methods, including prior basket delivery catheters. As explained above, prior catheters may only be introduced onto guidewires by unlocking the guidewire from its locking device and inserting the distal end of the catheter onto the proximal tip of the guidewire. This unlocking of the guidewire can result in movement or displacement of the distal end of the guidewire and thus loss of access to the treatment site. This insertion process is also time- and energy-consuming for the physician or practitioner. In contrast, according to various embodiments of the present disclosure, an exemplary catheter may be merged onto a guidewire via the slit in the saddle, while the guidewire remains locked in the locking device of the endoscopic block and while an endoscopic tool, such as a basket, is constrained within the sheath. The catheter may then be delivered to the desired treatment site via the guidewire, where the basket may be advanced to assume the expanded configuration. The expanded basket may then be utilized for one or more endoscopic procedures, such as the retrieval of gallstones. The basket may be withdrawn into the sheath and the catheter may be removed from the treatment site and split off of the guidewire. Advantageously, exemplary apparatuses, systems, and methods may allow the guidewire to remain locked during catheter insertion, basket use, and removal, thus ensuring that access to the desired treatment site is maintained. Additionally, merging of the catheter onto the guidewire via the slit in the saddle may be easier to perform and may require less time than the merging of prior devices.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An apparatus for merging a catheter onto a guidewire, the apparatus comprising:
    a catheter comprising:
       a flexible, elongated sheath configured to slidably receive an endoscopic tool therein, and
       a saddle secured to the sheath, the saddle including a guidewire lumen, wherein the guidewire lumen includes a slit extending along an axial length of the saddle; and
    an adapter configured to merge the catheter onto a guidewire, the adapter comprising:
       an adapter lumen configured to receive the catheter, the adapter lumen including:
          a first working channel configured to receive the sheath,
          a second working channel configured to receive the saddle, and
          a narrowed lumen portion situated between the first working channel and the second working channel, and
       a wedge extending from an inner surface of the adapter lumen into the second working channel, the wedge configured to widen a portion of the slit such that a portion of the guidewire merges into the guidewire lumen of the saddle through the widened portion of the slit.

2. The apparatus of claim 1,
    wherein the first working channel has a first radius and the second working channel has a second radius, the first radius being larger than the second radius.

3. The apparatus of claim 1, wherein the slit of the guidewire lumen is situated opposite the sheath about a circumference of the saddle.

4. The apparatus of claim 1, wherein a natural width of the slit of the guidewire lumen is smaller than the diameter of the guidewire.

5. The apparatus of claim 1,
    wherein an axial length of the sheath is longer than an axial length of the saddle, and
    wherein the saddle is secured to a distal portion of the sheath such that the sheath extends in a proximal direction beyond the proximal saddle end.

6. The apparatus of claim 1, wherein the endoscopic tool is an expandable retrieval basket.

7. The apparatus of claim 6, wherein the sheath is configured to retain the basket within an inner lumen thereof while the basket is in a closed configuration.

8. The apparatus of claim 1, wherein the sheath is configured as a first cylinder and the saddle is configured as a second cylinder, the first cylinder and second cylinder being secured at a point of connection between the sheath and the saddle such that a cross-section of the catheter has a figure-eight shape.

9. The apparatus of claim 1, wherein the adapter comprises:
    a side groove extending along an outer surface of the adapter, the side groove configured to receive a middle portion of the guidewire and to lead the guidewire towards the adapter lumen.

10. The apparatus of claim 1, wherein the widened portion of the slit is configured to return to a natural width after passing by the wedge such that the portion of the guidewire is retained within the saddle.

11. The apparatus of claim 1, wherein the adaptor is configured to be fixedly or removably engaged with an endoscopic block, the block configured to retain one or more guidewires.

12. The apparatus of claim 1, wherein the adaptor further comprises at least one holder configured to hold at least a portion of the catheter.

13. A method for merging a catheter onto a guidewire, the method comprising:
    obtaining a catheter, the catheter including:
       a flexible, elongated sheath configured to slidably receive an endoscopic tool therein, and
       a saddle secured to the sheath, the saddle including a guidewire lumen, wherein the guidewire lumen includes a slit extending along an axial length of the saddle;
    obtaining an adapter configured to merge the catheter onto a guidewire, the adapter comprising:
       an adapter lumen configured to receive the sheath and the saddle, the adapter lumen including a first working channel, a second working channel, and a narrowed lumen portion situated between the first working channel and the second working channel, and
       a wedge extending from an inner surface of the adapter lumen into the second working channel;
    receiving the sheath within the first working channel of the adapter lumen and receiving the saddle within the second working channel of the adapter lumen such that the wedge engages and widens a portion of the slit; and
    merging a portion of the guidewire into the guidewire lumen of the saddle through the widened portion of the slit.

14. The method of claim 13, wherein merging the portion of the guidewire into the guidewire lumen comprises merging the portion of the guidewire into a distal portion of the guidewire lumen.

15. The method of claim 14, further comprising:
    passing the catheter over the wedge and onto the guidewire until the entire length of the guidewire lumen is merged onto the guidewire.

16. The method of claim 15, further comprising:
    passing the sheath through the adapter lumen until a distal end of the sheath reaches a desired treatment site.

17. The method of claim 13, further comprising:
    extending the endoscopic tool beyond a distal tip of the sheath, wherein the endoscopic tool is configured to assume an expanded configuration when the endoscopic tool is removed from the sheath; and
    capturing a body with the expanded endoscopic tool.

18. The method of claim 13, further comprising:
    before merging the portion of the guidewire into the saddle, engaging the adapter with an opening of an endoscopic block, wherein the guidewire is retained by the endoscopic block.

19. The method of claim 13, further comprising:
    receiving a middle portion of the guidewire within a side groove extending along an outer surface of the adapter, the side groove being configured to lead the guidewire towards the adapter lumen.

20. An apparatus for merging a catheter onto a guidewire, the apparatus comprising:

a catheter comprising:
- first means for slidably receiving an endoscopic tool, and
- a saddle secured to the first means, the saddle including a guidewire lumen having second means for receiving a guidewire; and third means for receiving a middle portion of the guidewire while a proximal portion of the guidewire remains locked and for merging the saddle onto the guidewire.

* * * * *